United States Patent
Shin et al.

(10) Patent No.: US 12,387,323 B2
(45) Date of Patent: Aug. 12, 2025

(54) METHOD FOR TRACKING TUMOR IN CT IMAGE AND SYSTEM FOR DIAGNOSING USING THE SAME

(71) Applicant: ONCOSOFT INC., Chuncheon-si (KR)

(72) Inventors: Sang Joon Shin, Seoul (KR); Jin Sung Kim, Seoul (KR); Joon Seok Lim, Seoul (KR); Jee Suk Chang, Seoul (KR); Min Cheol Han, Seoul (KR); Seong Gong Moon, Seoul (KR)

(73) Assignee: ONCOSOFT INC., Chuncheon-si (KR)

( * ) Notice: Subject to any disclaimer, the term of this patent is extended or adjusted under 35 U.S.C. 154(b) by 406 days.

(21) Appl. No.: 18/064,032

(22) Filed: Dec. 9, 2022

(65) Prior Publication Data

US 2023/0162358 A1 May 25, 2023

Related U.S. Application Data

(63) Continuation of application No. PCT/KR2021/007295, filed on Jun. 10, 2021.

(30) Foreign Application Priority Data

Jun. 12, 2020 (KR) .................. 10-2020-0071460

(51) Int. Cl.
*G06T 7/00* (2017.01)
*G16H 30/20* (2018.01)

(52) U.S. Cl.
CPC ........... *G06T 7/0012* (2013.01); *G16H 30/20* (2018.01); *G06T 2200/08* (2013.01); *G06T 2207/10081* (2013.01); *G06T 2207/30096* (2013.01)

(58) Field of Classification Search
CPC .............. G06T 7/0012; G06T 2200/08; G06T 2207/10081; G06T 2207/30096; G16H 30/20
See application file for complete search history.

(56) References Cited

U.S. PATENT DOCUMENTS

| | | |
|---|---|---|
| 1,024,061 A | 4/1912 | Clark |
| 9,075,907 B2 | 7/2015 | Fujimoto |
| 10,922,874 B2 | 2/2021 | Lee et al. |
| 2008/0183069 A1 | 7/2008 | Fujimoto |

(Continued)

FOREIGN PATENT DOCUMENTS

| | | |
|---|---|---|
| JP | 2008-206969 A | 9/2008 |
| JP | 2012-513279 A | 6/2012 |

(Continued)

OTHER PUBLICATIONS

International Search Report issued in PCT/KR2021/007295; mailed Sep. 17, 2021.

*Primary Examiner* — Shefali D Goradia
(74) *Attorney, Agent, or Firm* — Studebaker Brackett PLLC

(57) ABSTRACT

The present disclosure relates to a method for tracking a tumor in a CT image and a system for diagnosing using the same. The method for tracking tumor includes the operations of: generating a 3D modeling image including at least one characteristic area in a subject's body based on the CT image of the subject; tracking a change according to a flow of time in the 3D modeling image with respect to the subject's characteristic area to generate time series data; and schematizing the time series data.

9 Claims, 15 Drawing Sheets

(56) References Cited

U.S. PATENT DOCUMENTS

| | | | |
|---|---|---|---|
| 2011/0268336 A1 | 11/2011 | Dmitrieva et al. | |
| 2016/0125640 A1 | 5/2016 | Lee et al. | |
| 2017/0116762 A1 | 4/2017 | Lin et al. | |
| 2020/0005496 A1 | 1/2020 | Lin et al. | |
| 2020/0098117 A1* | 3/2020 | Kask | G16H 50/50 |
| 2020/0113541 A1 | 4/2020 | Kato | |
| 2022/0143105 A1* | 5/2022 | Kong | A61K 35/74 |

FOREIGN PATENT DOCUMENTS

| | | |
|---|---|---|
| JP | 2019-000387 A | 1/2019 |
| KR | 10-2016-0051161 A | 5/2016 |

\* cited by examiner

FIG. 9A
FIG. 9B
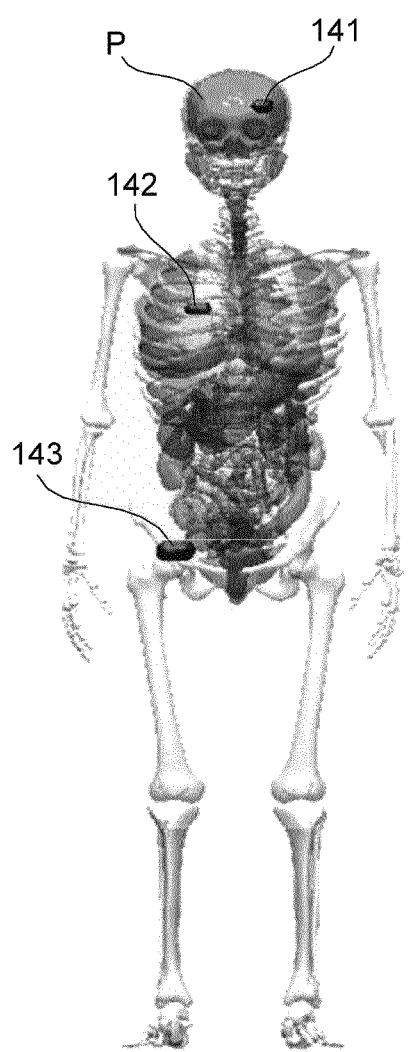
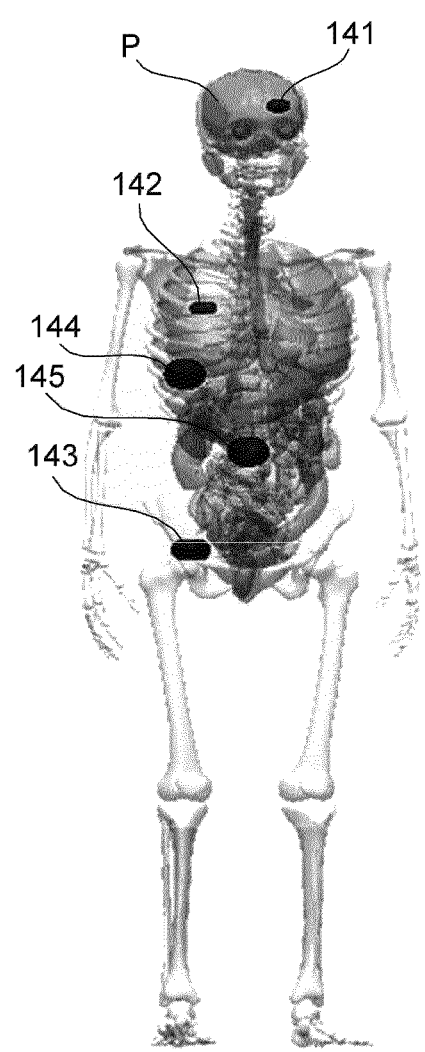

Contoured image

Surface volume

METHOD FOR TRACKING TUMOR IN CT IMAGE AND SYSTEM FOR DIAGNOSING USING THE SAME

CROSS-REFERENCE TO RELATED APPLICATION

The present application is a continuation of International Patent Application No. PCT/KR2021/007295, filed on Jun. 10, 2021, which is based upon and claims the benefit of priority to Korean Patent Application No. 10-2020-0071460, filed on Jun. 12, 2020. The disclosures of the above-listed applications are hereby incorporated by reference herein in their entirety.

BACKGROUND

1. Technical Field

The present disclosure relates to a diagnosis system, and relates to a diagnosis system for confirming a change in progress of a tumor over time using a tomography image.

2. Description of Related Art

A patient's health condition and disease can be diagnosed through medical images by scanning and processing structural details, internal tissues, and fluid flow within the body using a medical imaging apparatus.

A clinical decision support system (CDSS) is a system for assisting in clinical decision-making during treatment by grafting individual characteristics of a patient to a computerized database in order to provide information optimized for diagnosis and treatment of a cancer patient, and a system deriving a survival rate through basic information relating to the cancer patient and presents a treatment decision support.

To reduce reading errors, it is necessary to track the size and the number of tumors and the occurrence of new lesions according to time series and to confirm a change in progress of a tumor over time.

SUMMARY

The present disclosure has been made to solve the above-mentioned problems occurring in the prior art, and in an aspect of the present disclosure, an object of the present disclosure is to provide a method for tracking a tumor in a CT image and a system for diagnosing using the same, wherein a processor generates a 3D modeling image including at least one characteristic area in a subject's body based on the CT image of the subject, tracks a change according to a flow of time in the 3D modeling image with respect to the subject's characteristic area to generate time series data, and schematizes the time series data, thereby confirming a change in progress of a tumor over time.

Furthermore, another object of the present disclosure is to confirm a change of tissues by matching an image of a subject to a computational human phantom image.

The aspects of the present disclosure are not limited to those mentioned above, and other aspects not mentioned herein will be clearly understood by those skilled in the art from the following description.

To accomplish the above-mentioned objects, according to an aspect of the present disclosure, there is provided a method for tracking a tumor in a CT image including the operations of: a processor generating a 3D modeling image including at least one characteristic area in a subject's body based on the CT image of the subject; tracking a change according to a flow of time in the 3D modeling image with respect to the subject's characteristic area to generate time series data; and schematizing the time series data.

Here, the characteristic area is an area including the subject's tumor and internal organs.

Here, the generating time series data by tracking a change according to a flow of time for the characteristic area includes: collecting 3D modeling images of the subject generated at each preset sampling time; generating event occurrence messages in a case in which a change in the characteristic area is detected by comparing the collected 3D modeling images; and generating the time series data by analyzing the event occurrence messages.

Here, in an operation of generating event occurrence messages in a case in which a change in the characteristic area is detected by comparing the collected 3D modeling images, event occurrence messages including change information of the characteristic areas and event occurrence time at which the corresponding change is detected are generated in a case in which the location of the characteristic area is changed, in a case in which the size of the characteristic area is changed, or in a case in which the number of the characteristic areas is changed by comparing the collected 3D modeling images.

Here, the generating the time series data by analyzing the event occurrence messages tracks the size and the number of tumors and the occurrence of a new lesion according to time series by using change information of the characteristic area included in the event occurrence messages.

Here, the generating the 3D modeling image includes: obtaining a cross-sectional image including the characteristic area in the subject's body after capturing the CT image of the subject; marking the characteristic area on the tomography image of the subject prepared on the basis of the cross-sectional image to generate a contour image; converting a file format of the contour image into a medical file format; matching the converted contour image into a computational phantom image to generate a full-body mapping image of the subject; and performing volume rendering of the full-body mapping image to generate a 3D modeling image for each characteristic area in the subject's body.

Here, the marking the characteristic area on the tomography image of the subject prepared on the basis of the cross-sectional image to generate a contour image includes: confirming at least one characteristic area on the cross-sectional image; and marking a contour for each characteristic area confirmed in the tomography image of the subject.

Here, the performing volume rendering of the full-body mapping image to generate a 3D modeling image for each characteristic area in the subject's body includes: performing volume rendering for each characteristic area marked on the full-body mapping image to generate a surface volume image; and matching the surface volume image to the prepared 3D computational phantom to generate a 3D modeling image.

Here, according to another aspect of the present disclosure, there is provided a system for diagnosing using a method for tracking a tumor in a CT image including: a memory storing one or more instructions; a processor performing the one or more instructions stored in the memory; and an output unit outputting diagnosis results, wherein the processor performs the operations of: generating a 3D modeling image including at least one characteristic area in a subject's body based on the CT image of the subject; tracking a change according to a flow of time in the 3D modeling image with respect to the subject's characteristic area to generate time series data; and schematizing the time series data.

Here, the characteristic area is an area including the subject's tumor and internal organs.

Here, the processor performs the operation of setting a treatment direction method for the subject on the basis of the schematized time series data.

Here, the processor performs the operations of: collecting 3D modeling images of the subject generated at each preset sampling time; generating event occurrence messages in a case in which a change in the characteristic area is detected by comparing the collected 3D modeling images; and generating the time series data by analyzing the event occurrence messages.

Here, the processor generates event occurrence messages including change information of the characteristic areas and event occurrence time at which the corresponding change is detected in a case in which the location of the characteristic area is changed, in a case in which the size of the characteristic area is changed, or in a case in which the number of the characteristic areas is changed by comparing the collected 3D modeling images.

Here, the processor tracks the size and the number of tumors and the occurrence of a new lesion according to time series by using change information of the characteristic area included in the event occurrence messages.

ADVANTAGEOUS EFFECTS

As described above, according to the embodiments of the present disclosure, the method for tracking a tumor in a CT image includes the operations of the processor generating a 3D modeling image including at least one characteristic area in a subject's body based on the CT image of the subject, tracking a change according to a flow of time in the 3D modeling image with respect to the subject's characteristic area to generate time series data, and schematizing the time series data, thereby confirming a change in progress of a tumor over time.

In addition, the process can confirm a change of tissues by matching an image of a subject to a computational human phantom image.

The advantages of the present disclosure are not limited to the above-mentioned advantages, and other advantages, which are not specifically mentioned herein, will be clearly understood by those skilled in the art from the following description.

BRIEF DESCRIPTION OF THE DRAWINGS

FIGS. 8A to 9B illustrate tracking of a 3D modeling image of a system for diagnosing using a method for tracking a tumor in a CT image according to an embodiment of the present disclosure.

DETAILED DESCRIPTION

Figure 1:
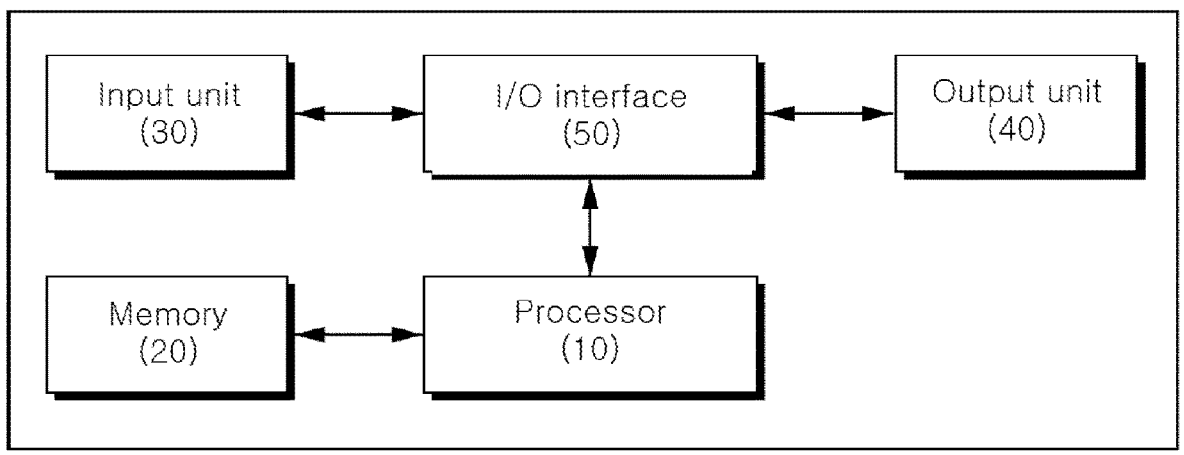
FIG. 1 is a block diagram of a system for diagnosing using a method for tracking a tumor in a CT image according to an embodiment of the present disclosure.

Hereinafter, a method for tracking a tumor in a CT image and a system for diagnosing using the same according to the present disclosure will be described in more detail with reference to the drawings. However, the present disclosure may be embodied in many different forms, and is not limited to the described embodiments. Additionally, in order to clearly describe the present disclosure, components irrelevant to the description are omitted, and the same reference numerals in the drawings indicate the same members.

The suffixes "module" and "unit" for the components used in the following description are given or used interchangeably in consideration of only the ease in writing the specification, and do not have meanings or roles distinguished from each other.

The present disclosure relates to a method for tracking a tumor in a CT image and a system for diagnosing using the same.

FIG. 1 is a block diagram of a system for diagnosing (hereinafter, called a 'diagnosis system') using a method for tracking a tumor in a CT image according to an embodiment of the present disclosure.

Referring to FIG. 1, a diagnosis system 1 using a method for tracking a tumor in a CT image according to an embodiment of the present disclosure includes a processor 10, a memory 20, an input unit 30, an output unit 40, and an I/O interface 50.

The diagnosis system 1 using the method for tracking a tumor in a CT image according to an embodiment of the present disclosure is a system for confirming a change of tumor over time using a tomography image of a subject and setting a treatment method.

A clinical decision support system (CDSS) is a system for helping clinical decision-making during treatment by grafting individual characteristics of a patient to a computerized database in order to provide information optimized for diagnosis and treatment of a cancer patient, and a system deriving the survival rate through basic information on the cancer patient and presents a treatment decision support.

To reduce reading errors, it is necessary to track the size and the number of tumors and the occurrence of new lesions according to time series and to confirm a change over time.

The diagnosis system 1 using the method for tracking a tumor in a CT image according to an embodiment of the present disclosure converts a change of the tumor over time into a graph by calculating the location, size, and number of tumors according to 3D modeling of a patient's CT image and segmentation of tumor and tracking the size and the number of tumors and the occurrence of new lesions according to time series.

Accordingly, the present disclosure may be applied to calculating a trend of a spontaneous change in tumors, and a trend of a change in tumors and dynamics according to pharmaceutical preparations, and to time series visualization and setting a treatment direction method.

The processor 10 performs: generating a 3D modeling image including at least one characteristic area in the subject's body based on the CT image of the subject; tracking a change according to a flow of time in the 3D modeling image with respect to the subject's characteristic area and generating time series data; and schematizing the time series data.

The processor 10 may be divided into a plurality of modules according to functions, or one processor may perform the functions.

The memory 20 may store programs (one or more instructions) for processing and controlling the processor 10.

The programs stored in the memory 20 may be divided into a plurality of modules according to functions, or an object type information recognition unit which will be described later may be composed of software modules.

In addition, the input unit 30 is a means allowing a user to input data for controlling the diagnosis system using the method for tracking a tumor in a CT image. The input unit 30 may be a key pad, a dome switch, a touch pad (a contact type capacitive type, a pressure type resistive type, an infrared sensing type, a surface ultrasonic conduction method, an integral tension measuring method, a piezo effect method, etc.), a jog wheel, a jog switch, and the like, but is not limited thereto.

The output unit 40 may display information on object recognition. For example, the output unit 40 may display a diagnosis result obtained from the processor 10.

The I/O interface 50 is a device capable of mounting a connection medium capable of connecting a system or equipment. In the present disclosure, the I/O interface 50 connects the processor to the input unit and the output unit.

Moreover, the diagnosis system may further include an imaging unit. The imaging unit captures a CT image of the subject to be diagnosed, and the processor 10 performs a method of generating a 3D modeling image of the subject from the CT image of the subject.

Hereinafter, the method for tracking a tumor in a CT image will be described in detail in FIGS. 2 to 4.

Figure 2:
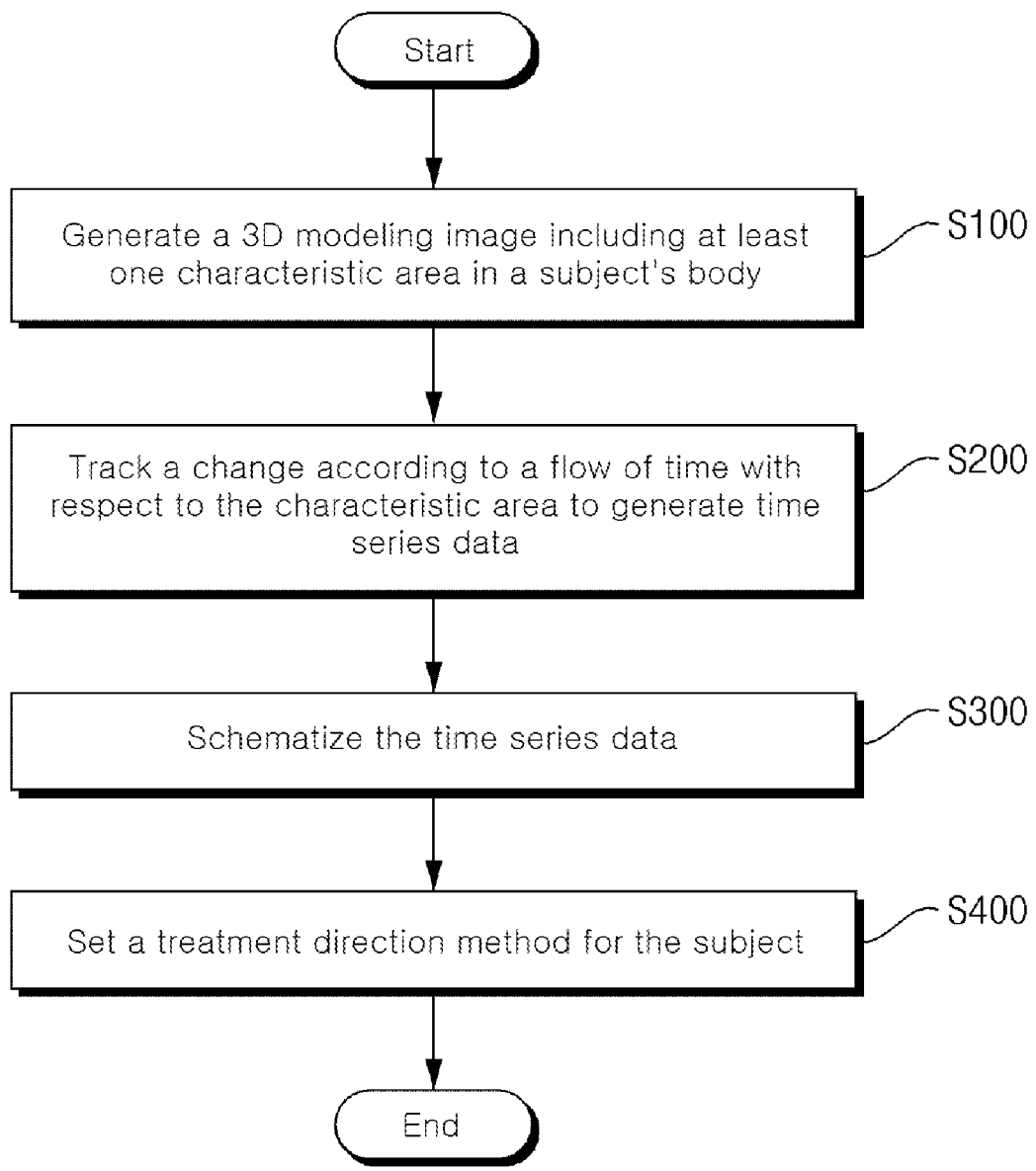
FIGS. 2 to 4 are flow charts for depicting a method for tracking a tumor in a CT image according to an embodiment of the present disclosure.
Figure 3:
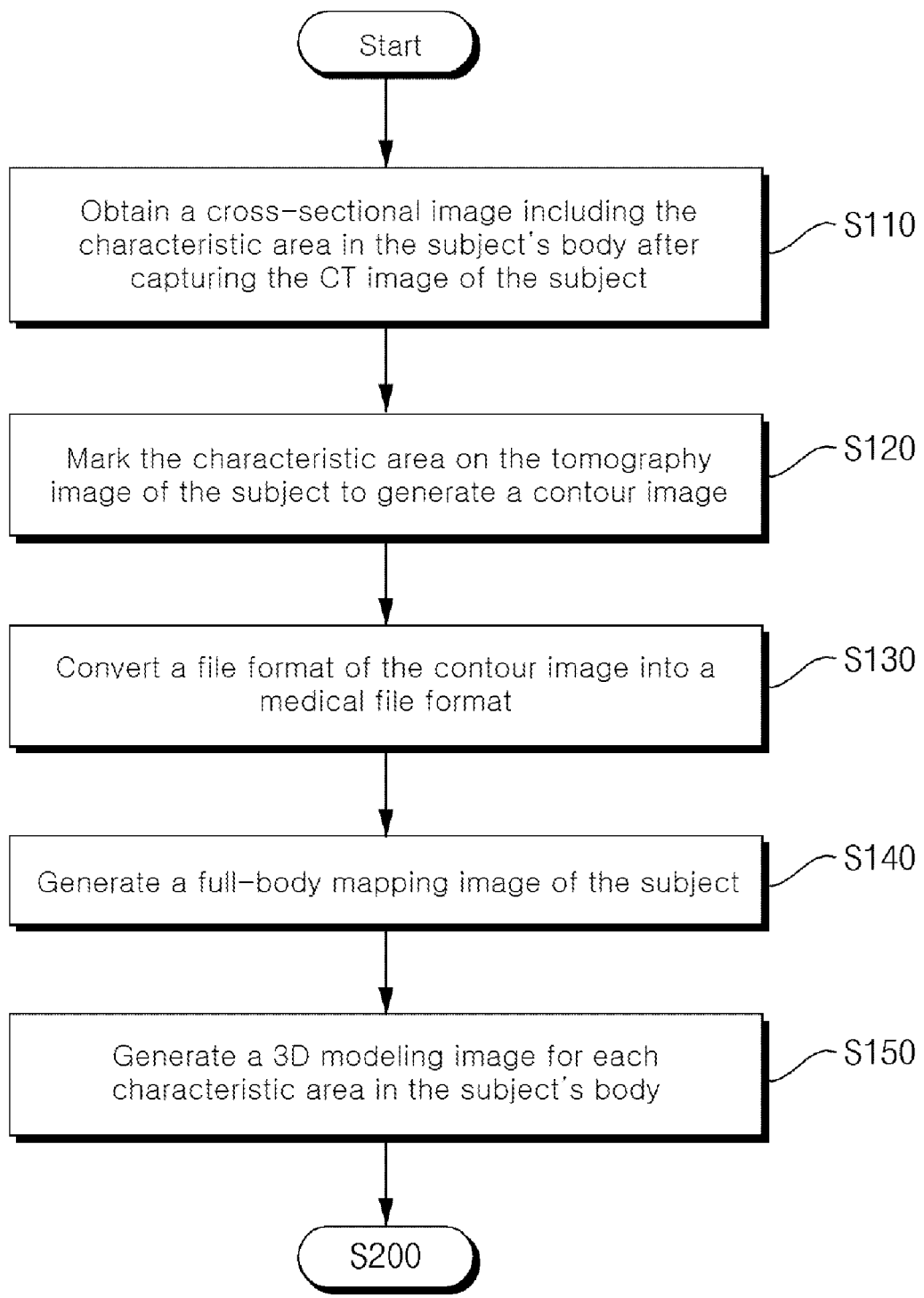
Figure 4:
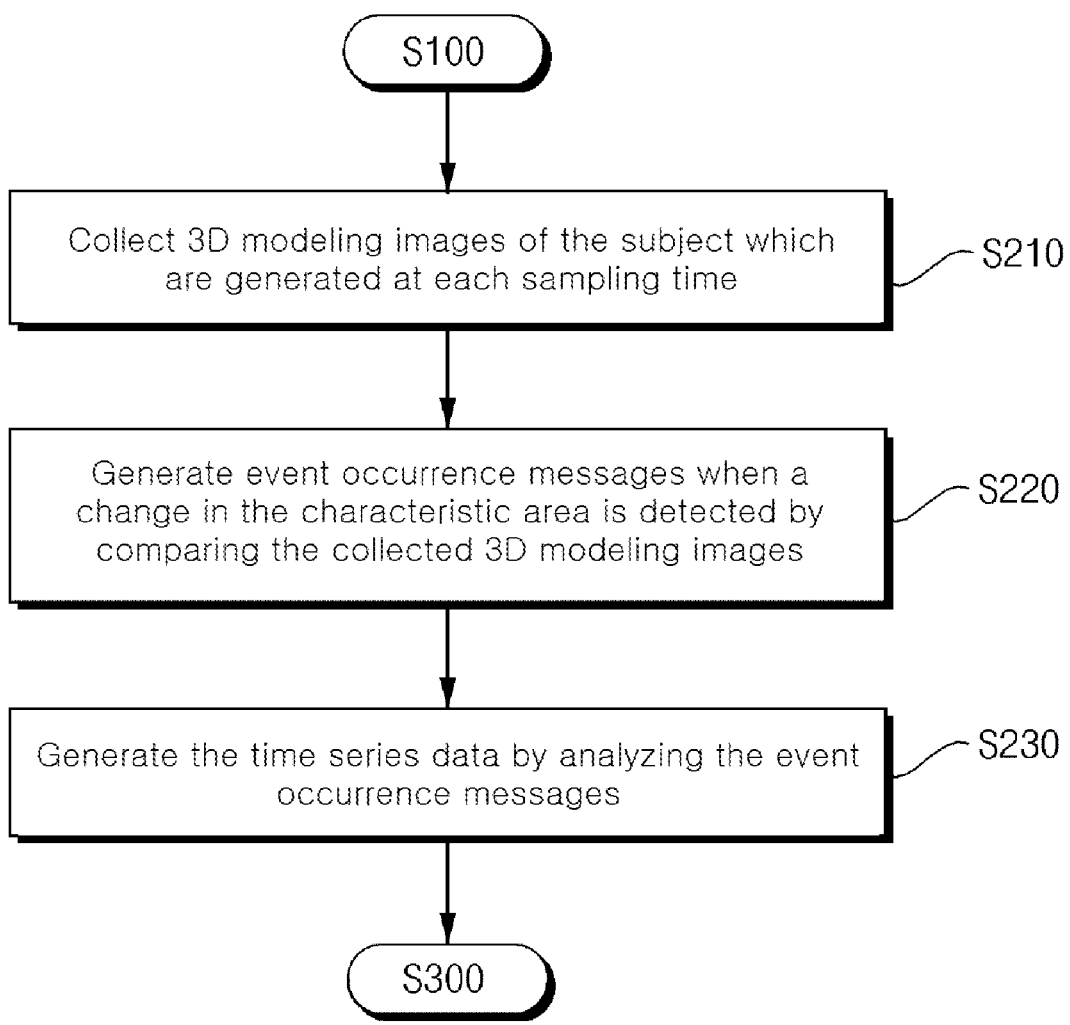

FIGS. 2 to 4 are flow charts for depicting a method for tracking a tumor in a CT image according to an embodiment of the present disclosure.

Referring to FIG. 2, the method for tracking a tumor in a CT image according to an embodiment of the present disclosure starts the operation S100 of generating a 3D modeling image including at least one characteristic area in the subject's body based on the CT image of the subject.

Here, the characteristic area is an area including the subject's tumor and internal organs.

In operation S200, the processor tracks a change according to a flow of time with respect to the subject's characteristic area in the 3D modeling image, and generates time series data.

In operation S300, the processor schematizes the time series data.

In operation S400, the processor sets a direction method for treatment of the subject based on the schematized time series data.

Referring to FIG. 3, the operation S100 of generating the 3D modeling image including at least one characteristic area in the subject's body based on the CT image of the subject in the method for tracking a tumor in a CT image according to an embodiment of the present disclosure includes the operation S110 that the processor obtains a cross-sectional image including the characteristic area in the subject's body after capturing the CT image of the subject.

Computed tomography (CT) is an imaging method that uses radiation like a chest X-ray scan, and captures the chest in cross section at regular intervals from the top to the bottom after a contrast agent is injected to scan the heart and the blood vessels.

Operation S120 includes: generating a contour image by marking the characteristic area on the subject's tomography image prepared on the basis of the cross-sectional image, and confirming at least one characteristic area in the cross-sectional image; and marking a contour for the characteristic area confirmed in the subject's tomography image.

Here, the characteristic area is an area including the subject's tumor and internal organs.

Specifically, the processor defines the patient's tumor and internal organs on the image and marks the same with colors in order to establish a radiation treatment plan from the captured cross-sectional image.

In operation S130, a file format of the contour image is converted into a medical file format.

Specifically, the tomography image and the contour formed thereon are exported in a DICOM format (respectively, (a DICOM image format and a DICOM RT-Structure format), which is a medical file format.

The contour image converted in operation S140 is matched to a computational phantom image to generate a full-body mapping image of the subject.

The operation S140 is an operation of matching the patient's image to well-made computational phantom images (CPs).

In general, a computational phantom image does not match a coordinate axis of a patient image, and does not match the height, weight, and locations of organs which are personal information of a patient. In operation S140, an actual image of the patient is matched to a phantom image by using technology of matching two images (e.g., template matching, (rigid or deformable) image registration, and the like).

Specifically, the scale of the contour image is converted according to the subject's body information to match the template thereof with that of the computational phantom image.

Thereafter, a difference in brightness values is calculated according to an area in which the template of the scale-converted contour image and the template of the computational phantom image overlap so as to search a matching location.

Here, to search the matching location is to change the location of the scale-converted contour image based on predetermined first parameter and second parameter, and to adjust the first parameter and the second parameter according to the difference in brightness values in the overlapping area.

For example, mapping of two images utilizing the template matching is a method of finding the smallest sum of absolute difference (SAD) while changing scales, locations, and the like of the two images.

In a case in which the intensities of the two images are respectively $l_s$ and $l_t$, the SAD is represented by the following Equation 1:

$$SAD(x, y) = \sum_{i=0}^{T_{rows}} \sum_{j=0}^{T_{cols}} \textit{Diff}(x+i, y+j, i, j) \quad \text{[Equation 1]}$$

where $\textit{Diff}(x_s, y_s, x_t, y_y) = |l_s(x_s, y_s) - l_t(x_t, y_t)|$, wherein x and y denote matching coordinates of the two images, and i and j denote a first parameter and a second parameter adjusted according to the difference in brightness values.

In operation S150, the method includes the operations of: generating a 3D modeling image according to a characteristic image in the body of the subject by performing the volume rendering of the full-body mapping image, and performing a volume rendering for each characteristic area marked in the full-body mapping image to generate a surface volume image; and matching the surface volume image to the prepared 3D computational phantom to generate a 3D modeling image.

Specifically, the processor performs volume rendering through contour information drawn on the patient tomography image to embody a surface volume (or 3D volume), and locates the converted surface volume on the pre-created 3D computational phantom to visualize it.

Here, the surface volume generated for each characteristic area is located on the 3D computational phantom according to the chronological sequence, so as to represent the change in location and size of tissues according to a flow of time on one phantom.

Referring to FIG. 4, in the method for tracking a tumor in a CT image according to an embodiment of the present disclosure, the operation S200 of generating time series data by tracking a change according to a flow of time for the characteristic area includes the operation S210 of collecting 3D modeling images of the subject generated at each preset sampling time.

In a case in which a change in the characteristic area is detected by comparing the 3D modeling images collected in operation S220, event occurrence messages are generated.

Specifically, in a case in which the location of the characteristic area is changed, in a case in which the size of the characteristic area is changed, or in a case in which the number of the characteristic areas is changed by comparing the collected 3D modeling images, event occurrence messages including change information of the characteristic areas and event occurrence time at which the corresponding change is detected are generated.

For example, the processor defines the patient's tumor and internal organs on the image and marks them by colors in order to establish a radiation treatment plan from the captured cross-sectional image. Accordingly, it is easy to confirm a change of tumor because only the change between the pieces of the marked information is confirmed.

In a case in which a newly marked area and the previously marked area have the same color but have different locations, it determined as the movement of the tumor, and the diagnosis time and the contents of the change are recorded.

In a case in which the marked area of a new modeling image is smaller or larger than the previously marked area, it is detected that there is a change in the tumor, and event occurrence messages are generated by recording the diagnosis time and the contents of the change.

In addition, in a case in which a new tumor appears and a new area is marked in addition to the previously marked information, event occurrence messages are generated by recording the diagnosis time and the contents of the change.

After event occurrence messages are generated and recorded according to the lapse of time, a lesion according to the contents of the change is diagnosed to generate time series data.

In operation S230, the event generation messages are analyzed to generate the time series data.

Specifically, the processor tracks the size and the number of tumors and the occurrence of a new lesion according to time series by using change information of the characteristic area included in the event occurrence message.

In the event occurrence message, the patient's condition is recorded in a case in which the size of the tumor is changed and in a case in which the location of the tumor is moved, and the occurrence of a new lesion is tracked in a case in which a new tumor appears.

Figure 5:
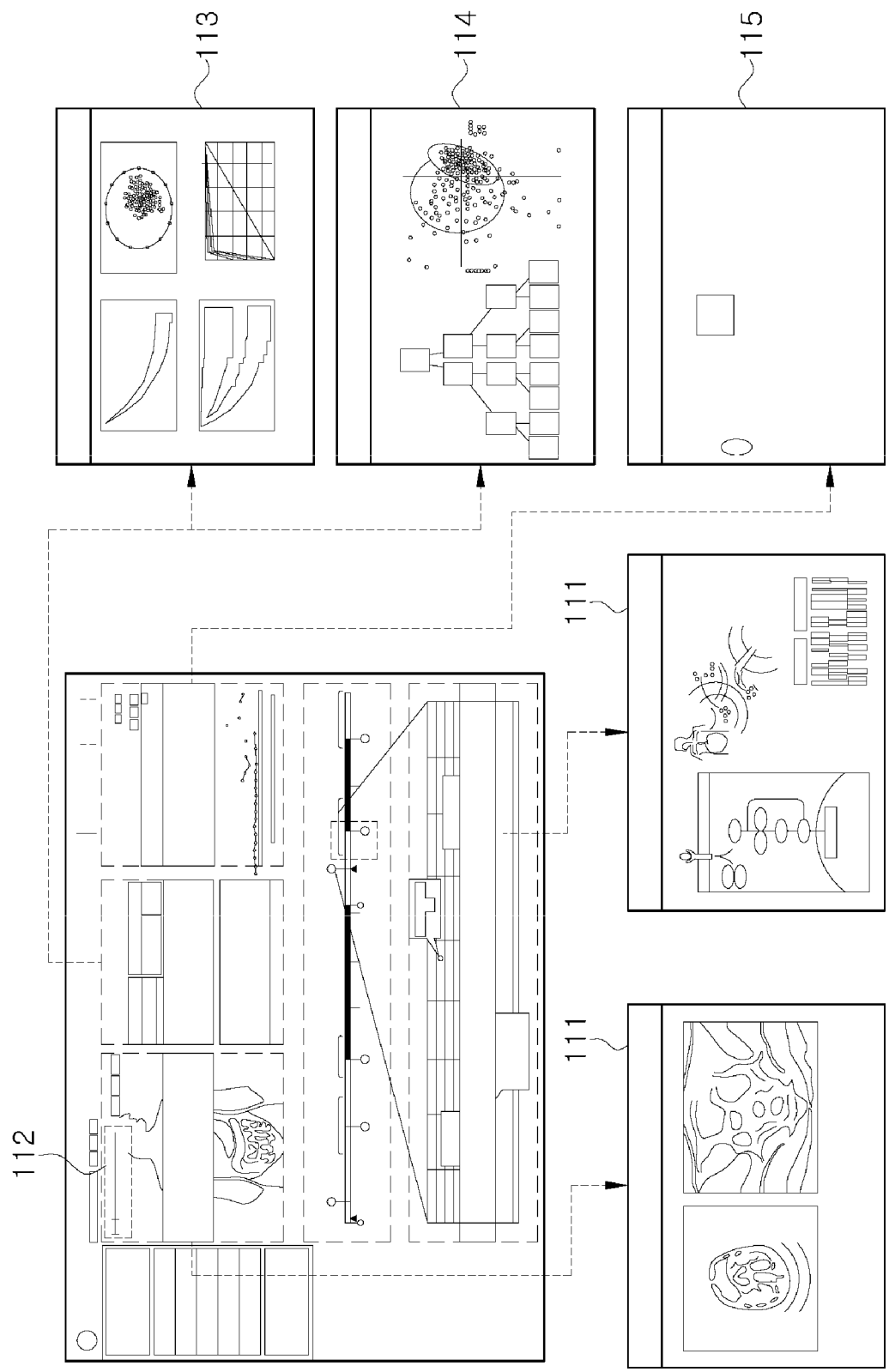
FIG. 5 illustrates a screen of a system for diagnosing using a method for tracking a tumor in a CT image according to an embodiment of the present disclosure.

FIG. 5 illustrates a screen of a diagnosis system using a method for tracking a tumor in a CT image according to an embodiment of the present disclosure.

The diagnosis system 1 using a method for tracking a tumor in a CT image according to an embodiment of the present disclosure uses a clinical decision support system (CDSS), and confirms the change of the tumor over time into a graph by calculating the location, size, and number of tumors according to 3D modeling of a patient's CT image and segmentation of tumor and tracking the size and the number of tumors and the occurrence of new lesions according to time series.

FIG. 5 illustrates a system for assisting clinical decision-making in treatment by grafting the individual characteristics of a patient to a computerized database to provide information optimized for diagnosis and treatment of cancer patients. The diagnosis system 1 using a method for tracking a tumor in a CT image according to an embodiment of the present disclosure can confirm time series changes in a patient diagnosis monitoring system since being capable of representing changes in the location and size of tissues according to a flow of time on a computational phantom.

Specifically, a 3D modeling image of the subject may be determined through a modeling image screen 111 of FIG. 5.

Since a sliding bar 112 capable of indicating the passage of time is displayed at the top of the modeling image screen 111, it is possible to confirm the change of the 3D modeling image according to the passage of time by dragging the sliding bar.

In addition, a graph screen showing time series data in a graph and a tree structure 113 are displayed.

The graph shows integrated test results of the subject, and tumor markers are illustrated in this embodiment.

Moreover, an information providing screen 114 provides customized knowledge-based medical information.

At the bottom, a timeline 115 of the subject is displayed, and the subject's condition is recorded according to a flow of time.

Figure 6:
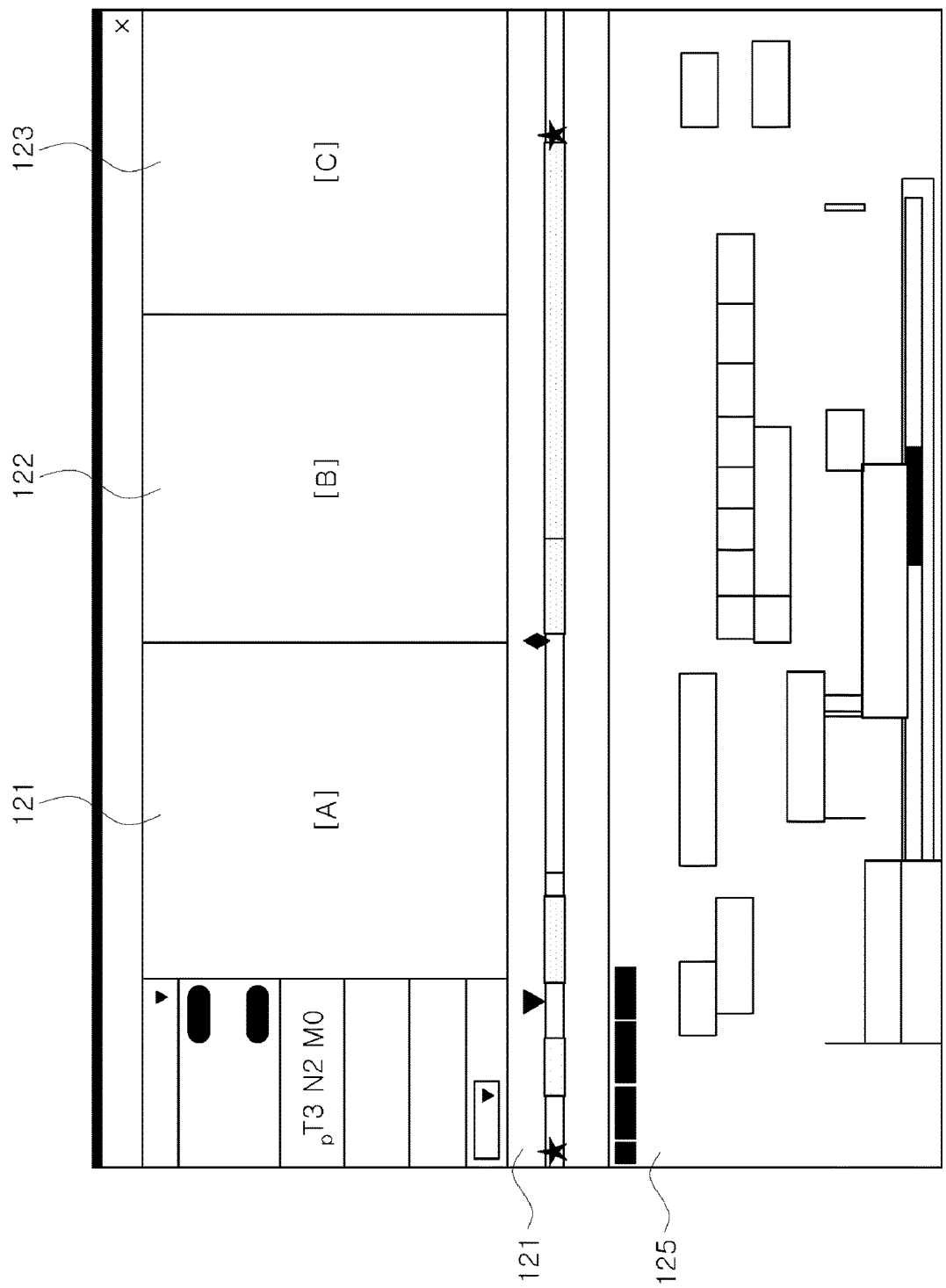
FIGS. 6 and 7 are views for depicting characteristics of a system for diagnosing using a method for tracking a tumor in a CT image according to an embodiment of the present disclosure.
Figure 7:
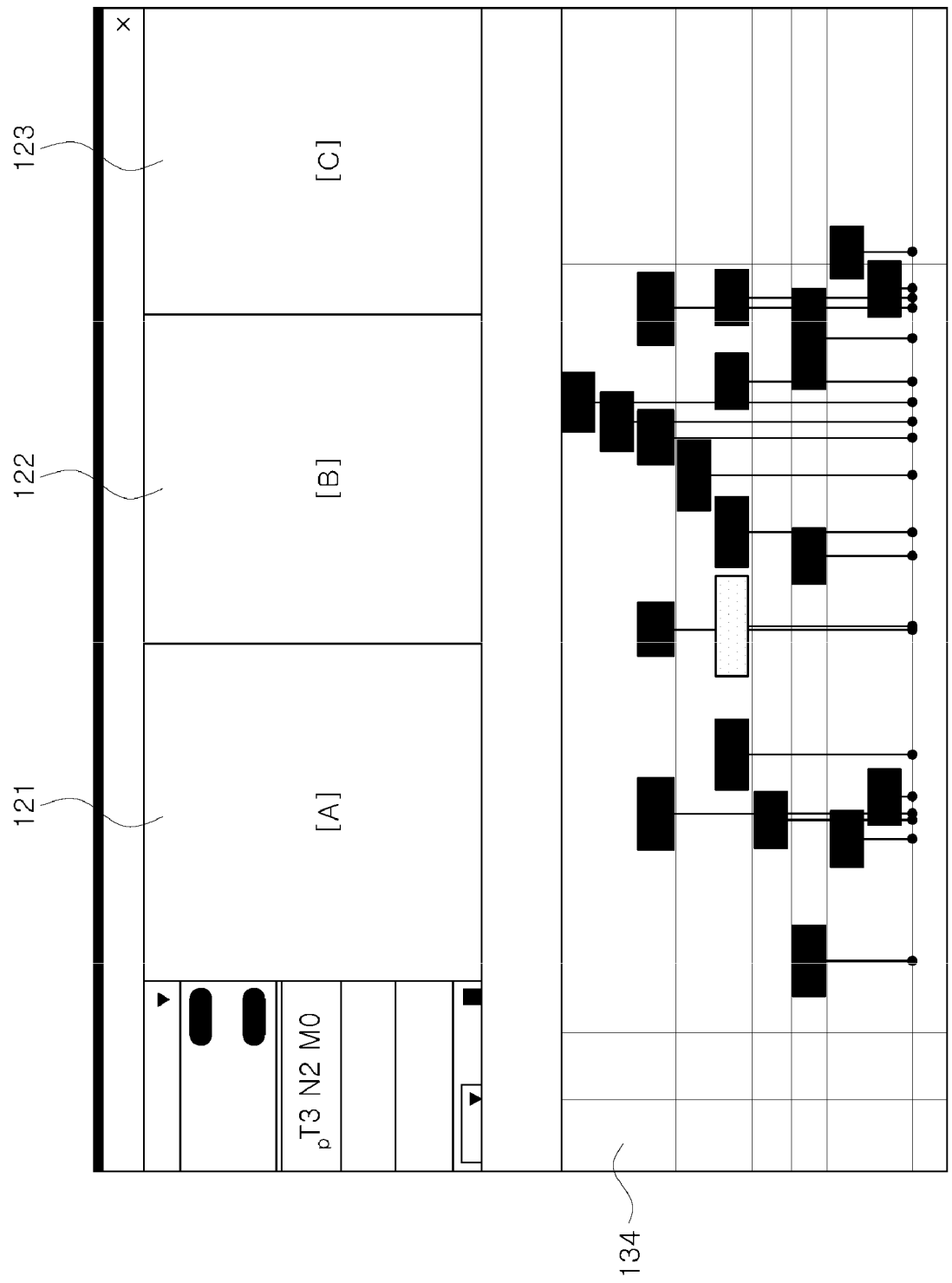

FIGS. 6 and 7 are views for depicting characteristics of a diagnosis system using a method for tracking a tumor in a CT image according to an embodiment of the present disclosure.

Referring to FIGS. 6 and 7, the diagnosis system using a method for tracking a tumor in a CT image according to an embodiment of the present disclosure includes modeling image display units 121 and 131, medical treatment support model display units 122 and 132, information providing units 123 and 133, and time series analysis units 124, 125 and 134.

The diagnosis system using a method for tracking a tumor in a CT image according to an embodiment of the present disclosure marks the location and morphological information of tumors on a 3D image according to a time series flow in treatment of the patient, thereby improving diagnosis and treatment effects.

The modeling image display units 121 and 131 marks the location and morphological information of tumors on a 3D image according to a time series flow in treatment of the patient, thereby increasing patient understanding of diagnosis and treatment effects. Accordingly, this enables a direct view of information, and facilitates communication between medical staff and patients.

In a case in which a video image vectorization system module is grafted to patient treatment through a new development of the video image vectorization system module, and generation of 3D modeling images including at least one characteristic area in the subject's body based on the CT image of the subject is repeated, only a change of the tumor according to the passage of time can be confirmed.

The treatment support model display units 122 and 132 develop a cancer patient treatment support model through a predictive model algorithm-based establishment. (Comparison of patient survival rate, development of recurrence risk algorithm according to treatment progress, etc.)

The processor can confirm a treatment strategy for a cancer patient, and determine a dynamic treatment regimen to propose bases for data-based survival, recurrence, and treatment.

Specifically, the processor confirms the treatment strategy using data according to the corresponding changes by comparing the collected 3D modeling mages, detecting a change in the characteristic area, and generating time series data to confirm the patient's lesion.

The information provision units 123 and 133 provide customized knowledge-based medical information. According to the present disclosure, it is possible to expand the diagnosis and treatment areas by using an artificial intelligence model and combining the existing data-based knowledge and the latest expert knowledge.

The time series analysis units 124, 125, and 134 construct cancer patient clinical data extraction and integrated data mining.

The processor facilitates improvement of speed/accuracy in diagnosis and treatment by standardizing cancer patient clinical bigdata, newly establishing a clinical information classification system, and visualizing time series information of patient data.

In a case in which a time series model of the cancer patient data is applied, it facilitates understanding of a status change form and prediction through the understanding of a status change form, and it is possible to confirm treatment information flow and confirmation of characteristics of the patient through with minimal data.

For example, referring to FIG. 6, the time series analysis units 124 and 125 sequentially record the patient's visit to the hospital, the patient's operation state, and results of image examination, functional examination, diagnostic examination, and pathological examination.

In addition, referring to FIG. 7, the time series analysis unit 134 displays the result of each diagnosis as a flag on the timeline.

FIGS. 8A to 9B illustrate tracking of a 3D modeling image of a diagnosis system using a method for tracking a tumor in a CT image according to an embodiment of the present disclosure.

Figure 8A:
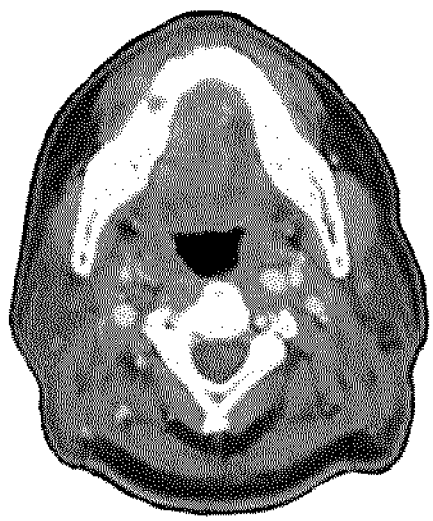
Figure 8B:
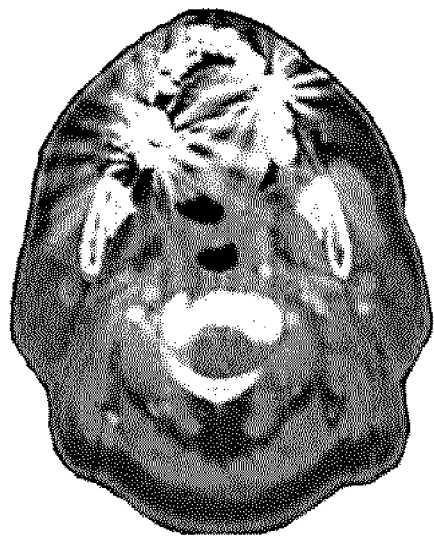

FIGS. 8A and 8B illustrate comparison between the existing images and the current images stored as time passes unlike the case where only the latest image is read.

Referring to FIG. 9, FIG. 9A illustrates tumors 141, 142, and 143 are initially displayed in the computational phantom P, and FIG. 9B illustrates a change in size of the existing tumors and new tumors 144 and 145 generated according to the flow of time in the computational phantom P.

Figure 10B:
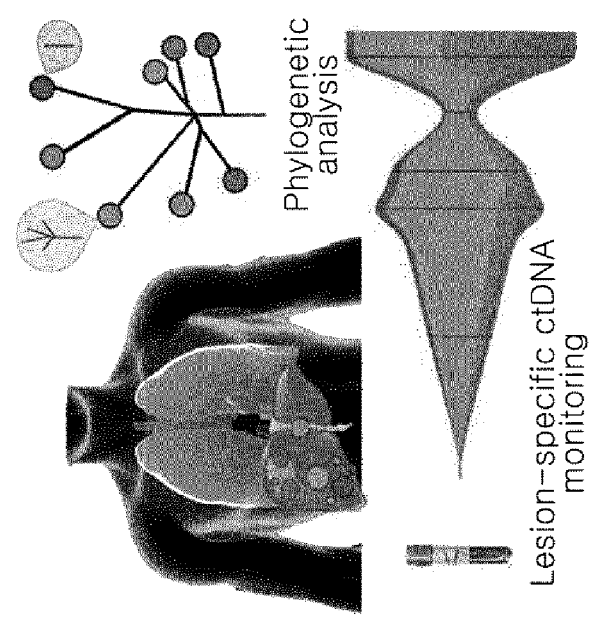
FIGS. 10A and 10B illustrate time series data of a system for diagnosing using a method for tracking a tumor in a CT image according to an embodiment of the present disclosure.
Figure 10A:
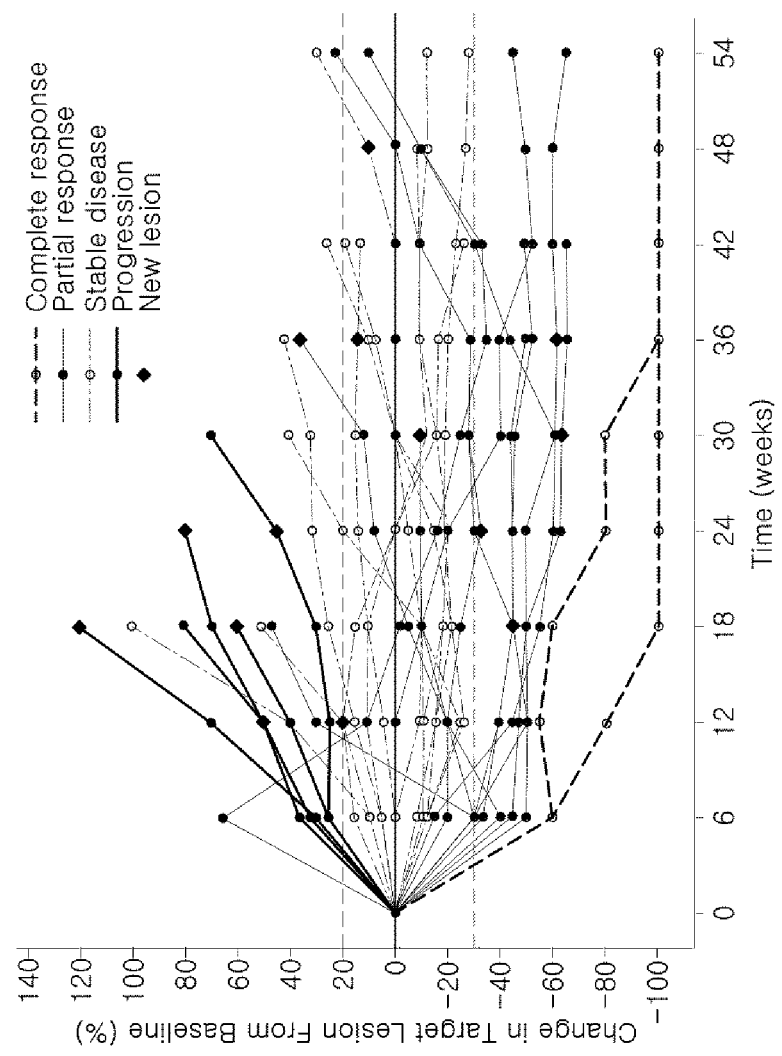

FIGS. 10A and 10B illustrate time series data of a diagnosis system using a method for tracking a tumor in a CT image according to an embodiment of the present disclosure.

FIG. 10A illustrates the change over time in a graph.

Specifically, FIG. 10A illustrates a change of a target lesion on the baseline according to the flow of time to confirm a complete response, a partial response, a progression, occurrence of a new lesion, etc.

FIG. 10B illustrates a process of tracking the size and the number of tumors and the occurrence of a new lesion according to time series.

Accordingly, the processor may set visualization according to time series and a treatment direction method using a trend of a spontaneous change in tumors, and a trend of a change in tumors and dynamics according to pharmaceutical preparations.

Figure 11B:
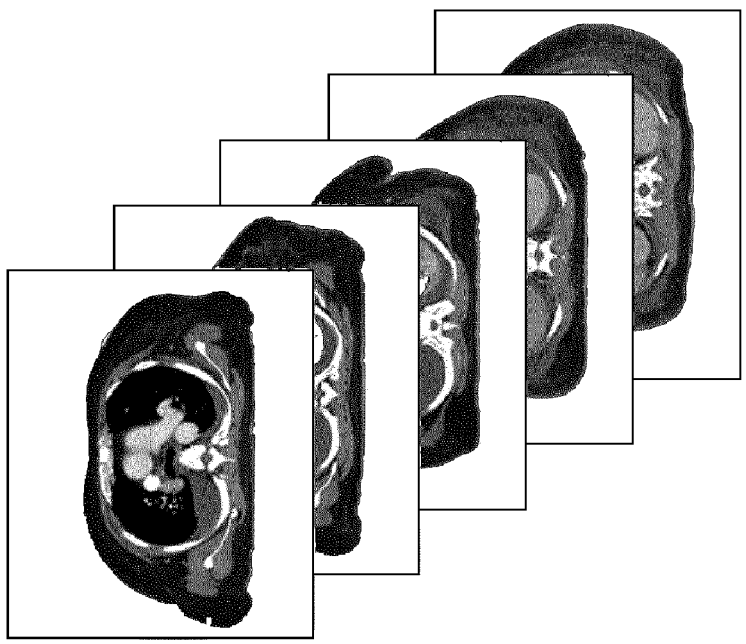
FIGS. 11A and 11B illustrate acquisition of a cross-sectional image of a method for tracking a tumor in a CT image according to an embodiment of the present disclosure and a system for diagnosing using the method.
Figure 11A:

FIGS. 11A and 11B illustrate acquisition of a cross-sectional image of a method for tracking a tumor in a CT image according to an embodiment of the present disclosure and a diagnosis system using the method.

As illustrated in FIG. 11A, the imaging unit captures a CT image of the subject to be diagnosed.

Computed tomography (CT) is an imaging method that uses radiation like a chest X-ray scan, and captures the chest in cross section at regular intervals from the top to the bottom after a contrast agent is injected to scan the heart and the blood vessels.

Since the image is obtained in a thin cross-section, it is easy to understand three-dimensional anatomical information, thereby expressing and diagnosing abnormality of the arterial arch or stricture of branches of blood vessels, such as temporal arteries, pulmonary veins, and pulmonary arteries which are hard to check with ultrasonic waves, in 3D composite images, and checking abnormalities of the airway, the lung, and other organs as well as the heart and the blood vessels.

As illustrated in FIG. 11B, the processor acquires a cross-sectional image including the characteristic area in the subject's body after capturing the CT image of the subject.

Here, the characteristic area is a region including the tumor and internal organs of the subject.

Figure 12:
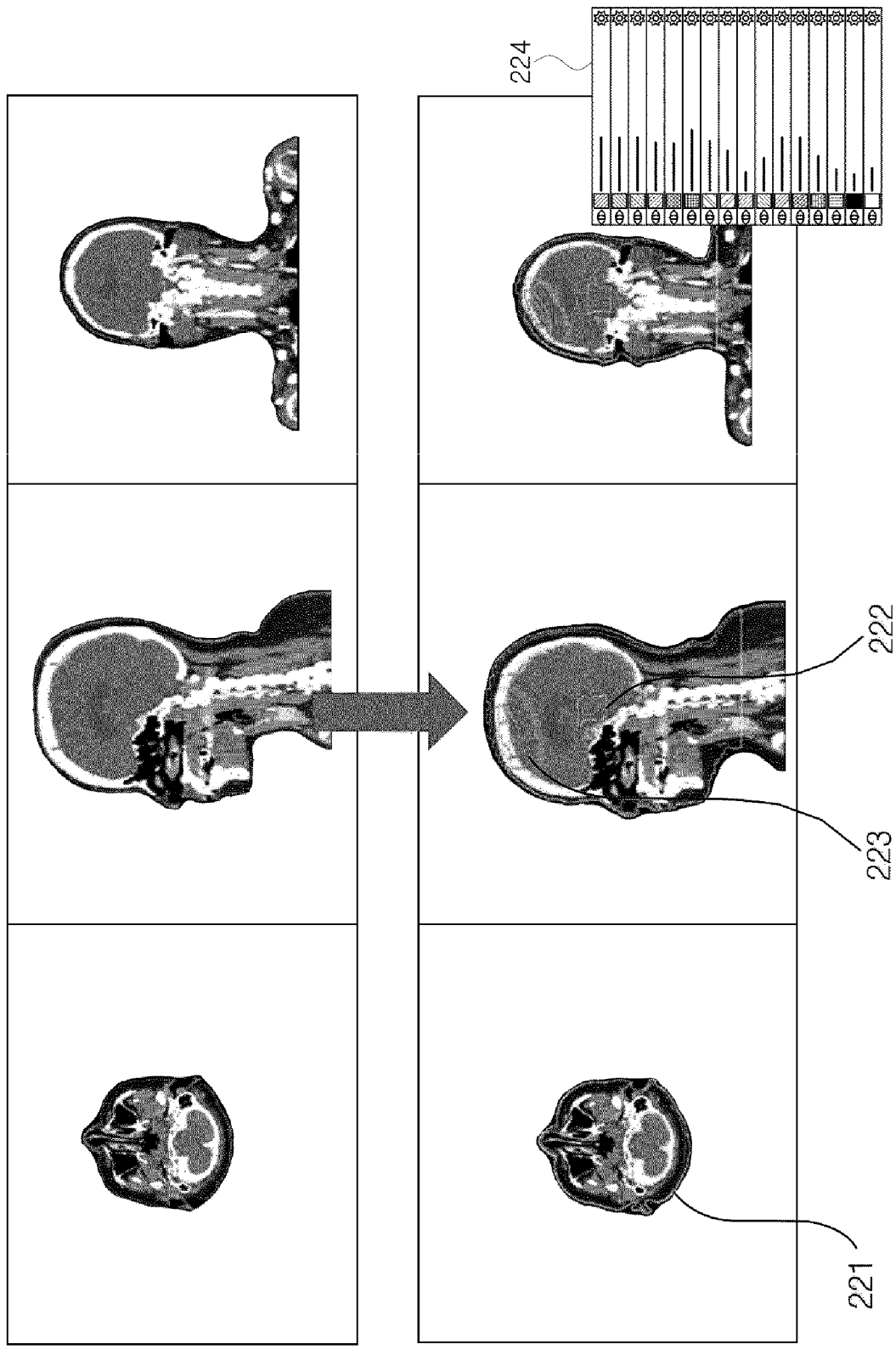
FIG. 12 illustrates generation of a contour image of a method for tracking a tumor in a CT image according to an embodiment of the present disclosure and a system for diagnosing using the method.

FIG. 12 illustrates generation of a contour image of a method for tracking a tumor in a CT image according to an embodiment of the present disclosure and a diagnosis system using the method.

As illustrated in FIG. 12, the processor marks the characteristic area on the pre-prepared tomography image of the subject based on the cross-sectional image to generate a contour image.

Here, the characteristic area is a region including the tumor and internal organs of the subject.

Specifically, the processor defines the patient's tumor and internal organs on the image and marks them by colors in order to establish a radiation treatment plan from the captured cross-sectional image.

For instance, a first characteristic area 221 corresponding to the external of the subject is marked on the tomography image of the subject, and a second characteristic area 222 corresponding to the brain stem is marked. Additionally, a third characteristic area 223 corresponding to the brain area may be marked, and the brain area includes hippocampus, optic chiasm, and fornix.

Locations of the characteristic areas of the subject can be displayed according to the marked colors through a marking table 224.

Figure 13A:
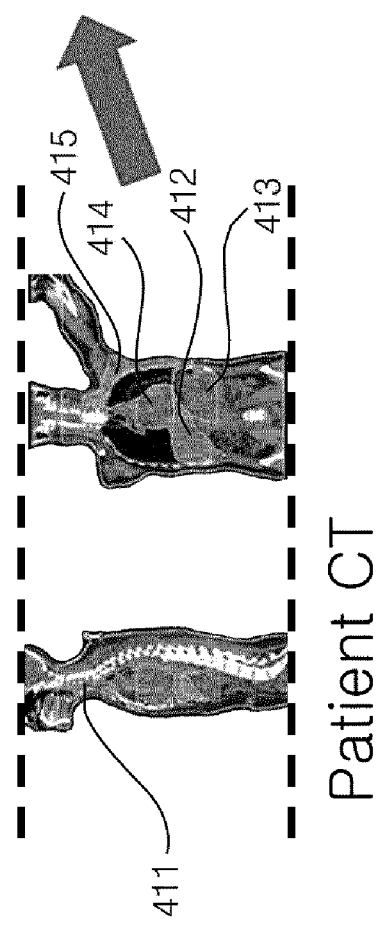
FIGS. 13A and 13B illustrate generation of a full-body mapping image of a method for tracking a tumor in a CT image according to an embodiment of the present disclosure and a system for diagnosing using the method.
Figure 13B:
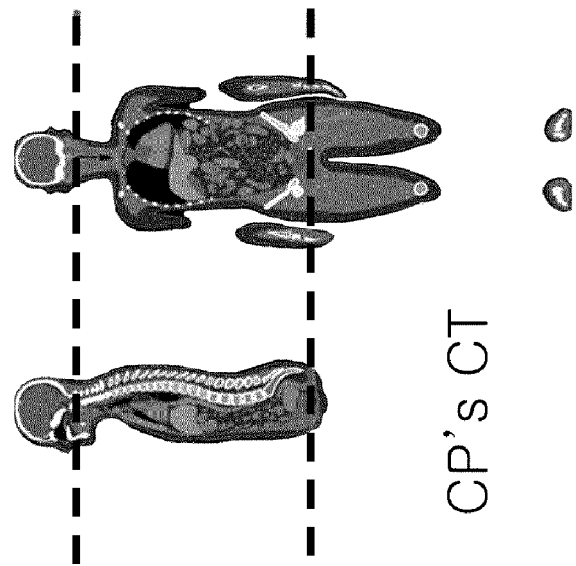

FIGS. 13A and 13B illustrate generation of a full-body mapping image of a method for tracking a tumor in a CT image according to an embodiment of the present disclosure and a diagnosis system using the method.

The processor converts the file format of the contour image into a medical file format. Specifically, the tomography image and the contour formed thereon are exported in a DICOM format (respectively, (a DICOM image format and a DICOM RT-Structure format), which is a medical file format.

Exporting means that a program using data in a special format stores its own data in a disk in a form that other programs can use. For example, data records of a database program can be stored in a disk in the form of an ASCII text file, and then, can be read and processed on a spreadsheet.

In a case in which the characteristic area is marked on the tomography image of the subject to generate a contour image, it is possible to check the locations of the characteristic areas of the subject according to the marked colors, and pieces of information on the characteristic areas matching the marked colors are converted and stored in a data table.

Thereafter, as illustrated in FIGS. 13A and 13B, the processor generates a full-body mapping image of the subject by matching the contour image to a computational phantom image, and the image of the subject is matched to well-made computational phantom images (CPs).

FIG. 13A is a patient image, and FIG. 13B is a patient image and a phantom image, which is a computational phantom image.

In general, a computational phantom image does not match a coordinate axis of a patient image, and does not match the height, weight, and locations of organs which are personal information of a patient. In operation S140, an actual image of the patient is matched to a phantom image by using technology of matching two images (e.g., template matching, (rigid or deformable) image registration, and the like).

Specifically, the scale of the contour image is converted according to the subject's body information to match the template thereof with that of the computational phantom image.

For example, a ratio is adjusted according to the subject's body information and the size of the computational phantom image.

Thereafter, a difference in brightness values is calculated according to an area in which the template of the scale-converted contour image and the template of the computational phantom image overlap so as to search a matching location. As illustrated in FIG. 13A, preferably, the scale-converted contour image is adjusted for each of the characteristic areas 411, 412, 413, 414, and 415 to match the computational phantom image.

Here, to search the matching location is to change the location of the scale-converted contour image based on predetermined first parameter and second parameter, and to adjust the first parameter and the second parameter according to the difference in brightness values in the overlapping area.

For example, mapping of two images utilizing the template matching uses a method of finding the smallest sum of absolute difference (SAD) while changing scales, locations, and the like of the two images, and can be calculated using the Equation 1.

Figure 14A:
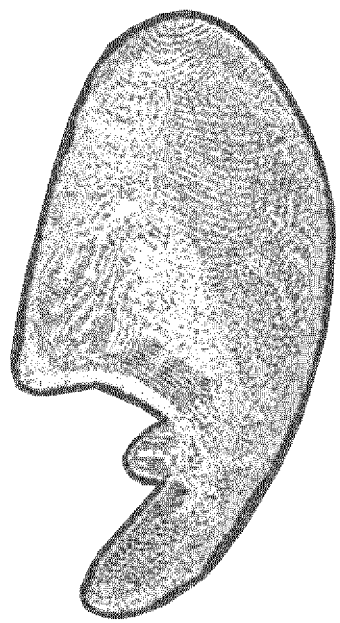
FIGS. 14A and 14B illustrate volume rendering of a method for tracking a tumor in a CT image according to an embodiment of the present disclosure and a system for diagnosing using the method.
Figure 14B:
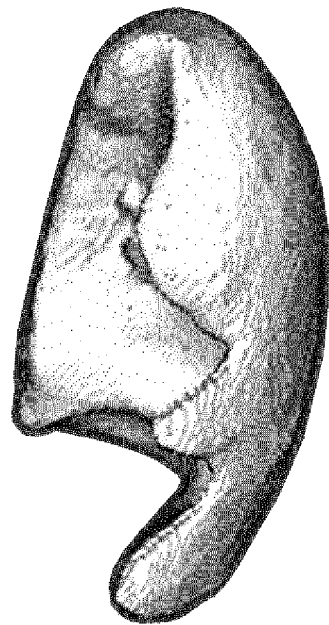

FIGS. 14A and 14B illustrate volume rendering of a method for tracking a tumor in a CT image according to an embodiment of the present disclosure and a diagnosis system using the method.

As illustrated in FIGS. 14A and 14B, the processor generates a surface volume image by performing volume rendering for each characteristic area marked on the full-body mapping image.

That is, the volume rendering is performed through the contour information drawn on the patient tomography image and is implemented as a surface volume (or 3D volume).

FIGS. 14A and 14B illustrate the surface volume of the lung generated through volume rendering. As illustrated in FIG. 9A, the contour image is implemented as a surface volume image as illustrated in FIG. 14B.

Volume rendering is a method applicable to a medical simulator performing procedures of diagnosing a disease or removing, cutting, or shaving tissues by showing medical image data as it is without filtering or segmentation, and is to extract useful image information from volume data to perform rendering.

Volume data is composed of basic elements called voxels, and each voxel may have unique density, opacity, color, and the like. Continuous cross-sectional images of the internal of the human body are obtained by a computerized tomography device, such as CT or MRI, and then, a three-dimensional structure of the human body is reconstructed, thereby making a virtual three-dimensional image similar to that seen with an endoscope camera.

Figure 15:
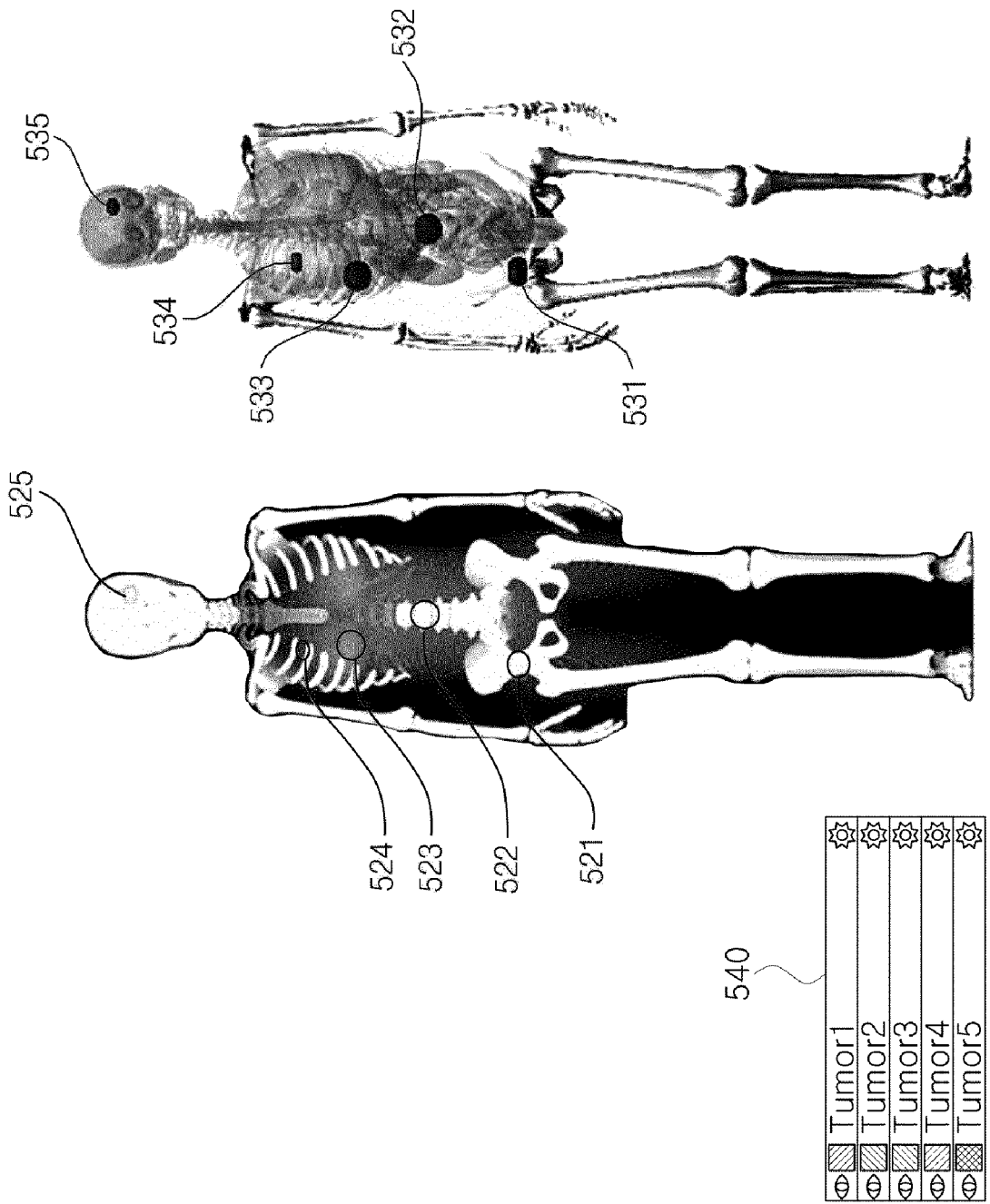
FIG. 15 illustrates generation of a 3D modeling image of a method for tracking a tumor in a CT image according to an embodiment of the present disclosure and a system for diagnosing using the method.

FIG. 15 illustrates generation of a 3D modeling image of a method for tracking a tumor in a CT image according to an embodiment of the present disclosure and a diagnosis system using the method.

As illustrated in FIG. 15, the processor generates a 3D modeling image by matching the surface volume images to pre-prepared 3D computational phantoms.

The converted surface volumes are located on the pre-generated 3D computational phantoms, and then, are visualized.

Referring to FIG. 15, surface volumes are generated for a first characteristic area 521, a second characteristic area 522, a third characteristic area 523, a fourth characteristic area 524, and a fifth characteristic area 525 marked for the characteristic area tables 540 to display a first characteristic area surface volume image 531, a second characteristic area surface volume image 532, a third characteristic area surface volume image 533, a fourth characteristic area surface volume image 534, and a fifth characteristic area surface volume image 535 of the pre-generated 3D computational phantoms.

In addition, the surface volume generated for each characteristic area is located on the 3D computational phantom in chronological order, it is possible to represent changes in the location and size of tissues according to a flow of time on one phantom.

It will be understood by those of ordinary skill in the art that the above embodiments of the present invention are just exemplified, and various changes, modifications and equivalents may be made therein without departing from the essential characteristics of the present disclosure. Therefore, the scope of the present disclosure should be construed to include various embodiments within the scope equivalent to those described in the claims without being limited to the above-described embodiments.

The invention claimed is:

1. A method for tracking a tumor in a Computed Tomography (CT) image, the method comprising:
generating a 3D modeling image including at least one characteristic area in a subject's body based on the CT image of the subject;
generating time series data by tracking a change according to a flow of time in the 3D modeling image with respect to the subject's characteristic area; and
schematizing the time series data,
wherein the generating of the time series data comprises:
collecting 3D modeling images of the subject generated at each preset sampling time;
generating event occurrence messages in a case in which a change in the characteristic area is detected by comparing the collected 3D modeling images; and
generating the time series data by analyzing the event occurrence messages,
wherein the generating of the event occurrence messages comprises:
generating the event occurrence messages including change information of the characteristic areas and event occurrence time at which the change in the characteristic area is detected, by detecting, by comparing the collected 3D modeling images, a case in which a location of the characteristic area is changed, a case in which a size of the characteristic area is changed, or a case in which a number of the characteristic areas is changed, and
wherein the generating of the time series data further comprises: tracking the size and the number of tumors and the occurrence of a new lesion according to time series, by using change information of the characteristic area included in the event occurrence messages.

2. The method according to claim 1, wherein the characteristic area is an area including the subject's tumor and internal organs.

3. A method for tracking a tumor in a Computed Tomography (CT) image, the method comprising:
generating a 3D modeling image including at least one characteristic area in a subject's body based on the CT image of the subject;
generating time series data by tracking a change according to a flow of time in the 3D modeling image with respect to the subject's characteristic area; and
schematizing the time series data,
wherein the characteristic area is an area including the subject's tumor and internal organs,
wherein the generating of the time series data comprises:
collecting 3D modeling images of the subject generated at each preset sampling time;
generating event occurrence messages in a case in which a change in the characteristic area is detected by comparing the collected 3D modeling images; and
generating the time series data by analyzing the event occurrence messages,
wherein the generating of the event occurrence messages comprises:
generating the event occurrence messages including change information of the characteristic areas and event occurrence time at which the change in the characteristic area is detected, by detecting, by comparing the collected 3D modeling images, a case in which a location of the characteristic area is changed, a case in which a size of the characteristic area is changed, or a case in which a number of the characteristic areas is changed, and
wherein the generating of the 3D modeling image comprises:
obtaining a cross-sectional image including the characteristic area in the subject's body after capturing the CT image of the subject;
marking the characteristic area on the CT image of the subject prepared based on the cross-sectional image to generate a contour image;
converting a file format of the contour image into a medical file format;
matching the converted contour image into a computational phantom image to generate a full-body mapping image of the subject; and
performing volume rendering of the full-body mapping image to generate a 3D modeling image for each characteristic area in the subject's body.

4. The method according to claim 3, wherein the marking of the characteristic area comprises:
confirming at least one characteristic area on the cross-sectional image; and
marking a contour for each characteristic area confirmed in the CT image of the subject.

5. The method according to claim 4, wherein the performing of the volume rendering comprises:
performing the volume rendering for each characteristic area marked on the full-body mapping image to generate a surface volume image; and
matching the surface volume image to the prepared 3D computational phantom to generate a 3D modeling image.

6. The method according to claim 3, wherein the characteristic area is an area including the subject's tumor and internal organs.

7. A system for diagnosing using a method for tracking a tumor in a Computed Tomography (CT) image, the system comprising:
a memory storing one or more instructions;
a processor performing the one or more instructions stored in the memory; and
an output unit outputting a diagnosis result,
wherein the processor is configured to perform:
generating a 3D modeling image including at least one characteristic area in a subject's body based on the CT image of the subject;
generating time series data by tracking a change according to a flow of time in the 3D modeling image with respect to the subject's characteristic area; and
schematizing the time series data,
wherein the processor is further configured to perform:
collecting 3D modeling images of the subject generated at each preset sampling time;
generating event occurrence messages in a case in which a change in the characteristic area is detected by comparing the collected 3D modeling images; and generating the time series data by analyzing the event occurrence messages, wherein the processor is further configured to perform:
generating the event occurrence messages including change information of the characteristic areas and event occurrence time at which the change in the characteristic area is detected, by detecting, by comparing the collected 3D modeling images, a case in which a location of the characteristic area is changed, a case in which a size of the characteristic area is changed, or a case in which a number of the characteristic areas is changed, and wherein the processor is further configured to perform:
tracking the size and the number of tumors and the occurrence of a new lesion according to time series, by using change information of the characteristic area included in the event occurrence messages.

8. The system according to claim 7, wherein the characteristic area is an area including the subject's tumor and internal organs.

9. The system according to claim 7, wherein the processor is further configured to perform: setting a treatment direction method for the subject, based on the schematized time series data.

* * * * *